United States Patent [19]

Mullani

[11] Patent Number: 4,563,582

[45] Date of Patent: Jan. 7, 1986

[54] POSITRON EMISSION TOMOGRAPHY CAMERA

[75] Inventor: Nizar A. Mullani, Houston, Tex.

[73] Assignee: Clayton Foundation for Research, Houston, Tex.

[21] Appl. No.: 613,699

[22] Filed: May 24, 1984

[51] Int. Cl.⁴ ............................................. G01T 1/164
[52] U.S. Cl. ................................ 250/363 S; 250/366; 250/367; 378/147
[58] Field of Search .................... 250/363 S, 367, 366, 250/363 R; 378/147

[56] References Cited

U.S. PATENT DOCUMENTS 4,394,576  7/1983  Tanaka et al. ...................... 250/366

FOREIGN PATENT DOCUMENTS 58-14071  1/1983  Japan .............................. 250/363 SA

OTHER PUBLICATIONS

Derenzo, "Detectors, Sampling, Shielding, and Electronics for Positron Emission Tomography", Lawrence Berkeley Lab, LBL-13091, 08-81.
Burnham et al., "A Multicrystal Positron Camera", IEEE Trans. Nucl. Sci., 19(3), Jun. 1972, pp. 201-205.

Primary Examiner—Carolyn E. Fields
Attorney, Agent, or Firm—Fulbright & Jaworski

[57] ABSTRACT

A positron emission tomography camera having a plurality of detector rings positioned side-by-side or offset by one-half of the detector cross section around a patient area to detect radiation therefrom. Each ring contains a plurality of scintillation detectors which are positioned around an inner circumference with a septum ring extending inwardly from the inner circumference along each outer edge of each ring. An additional septum ring is positioned in the middle of each ring of detectors and parallel to the other septa rings whereby the inward extent of all the septa rings may be reduced by one-half and the number of detectors required in each ring is reduced. Each detector ring or offset ring includes a plurality of photomultiplier tubes and a plurality of scintillation crystals are positioned relative to the photomultiplier tubes whereby each tube is responsive to more than one crystal. Each alternate crystal in the ring is offset by one-half or less of the thickness of the crystal such that the staggered crystals are seen by more than one photomultiplier tube. This sharing of crystals and photomultiplier tubes allows identification of the staggered crystal and the use of smaller detectors shared by larger photomultiplier tubes thereby requiring less photomultiplier tubes, creating more scanning slices, providing better data sampling, and reducing the cost of the camera. The offset detector ring geometry combined with the additional septa reduces the cost of the positron camera and improves its performance.

7 Claims, 15 Drawing Figures

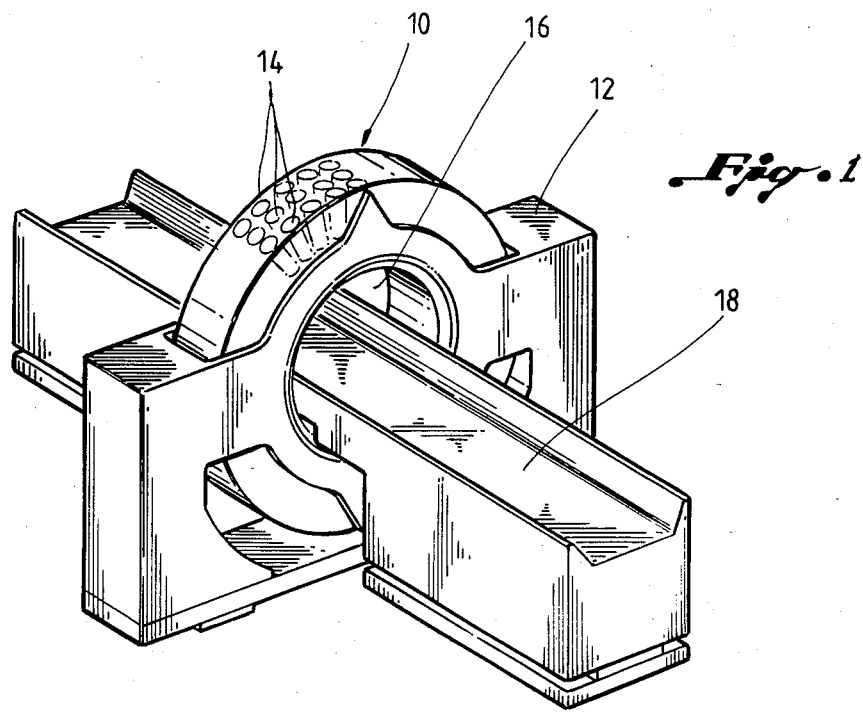
Fig. 1
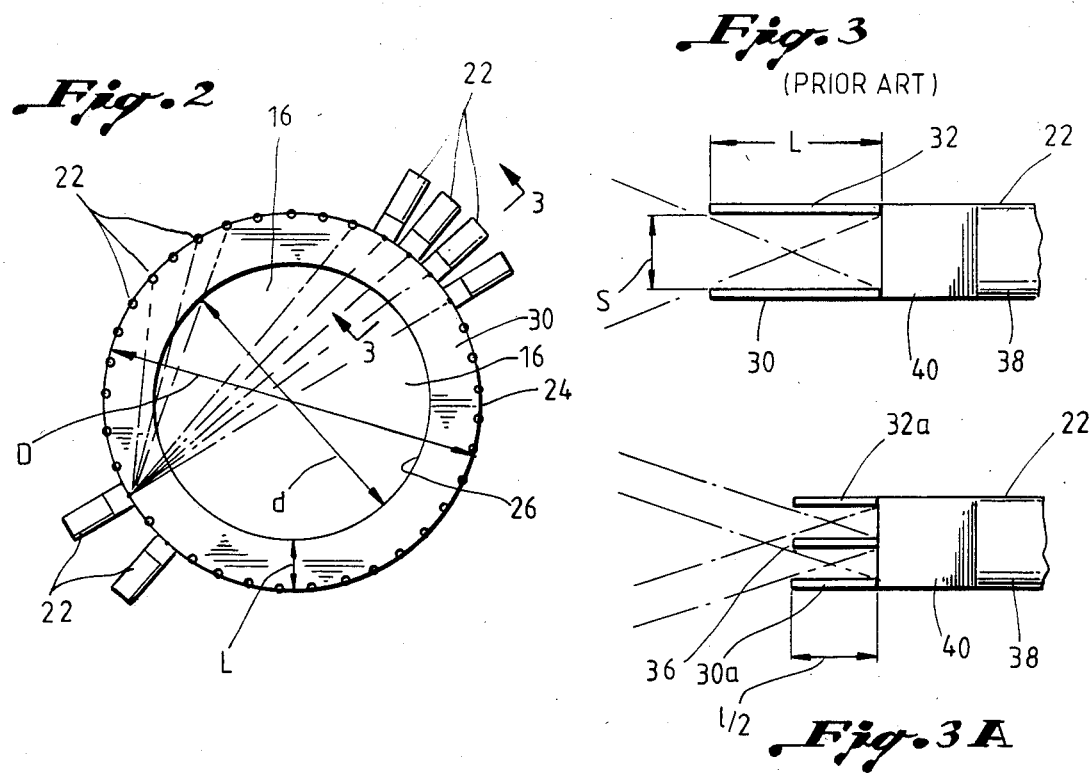
Fig. 2
Fig. 3 (PRIOR ART)
Fig. 3A

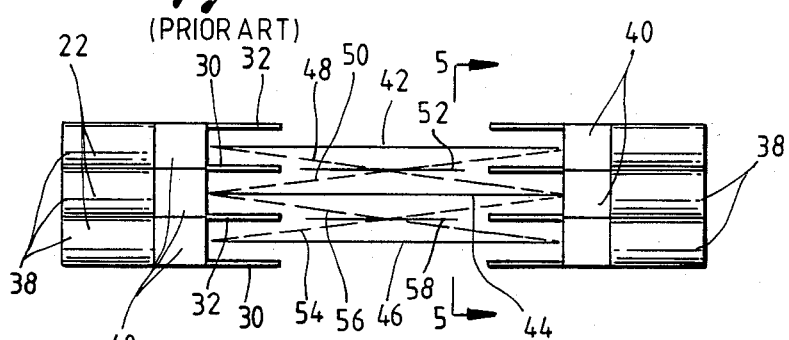
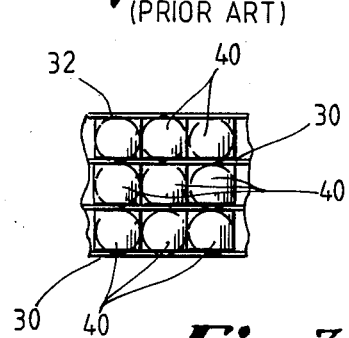
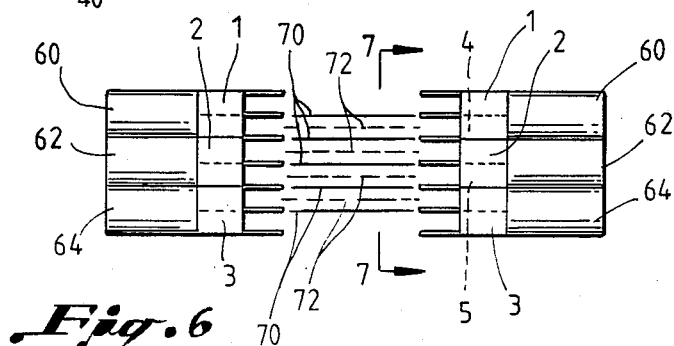
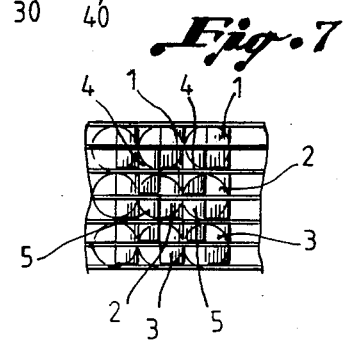
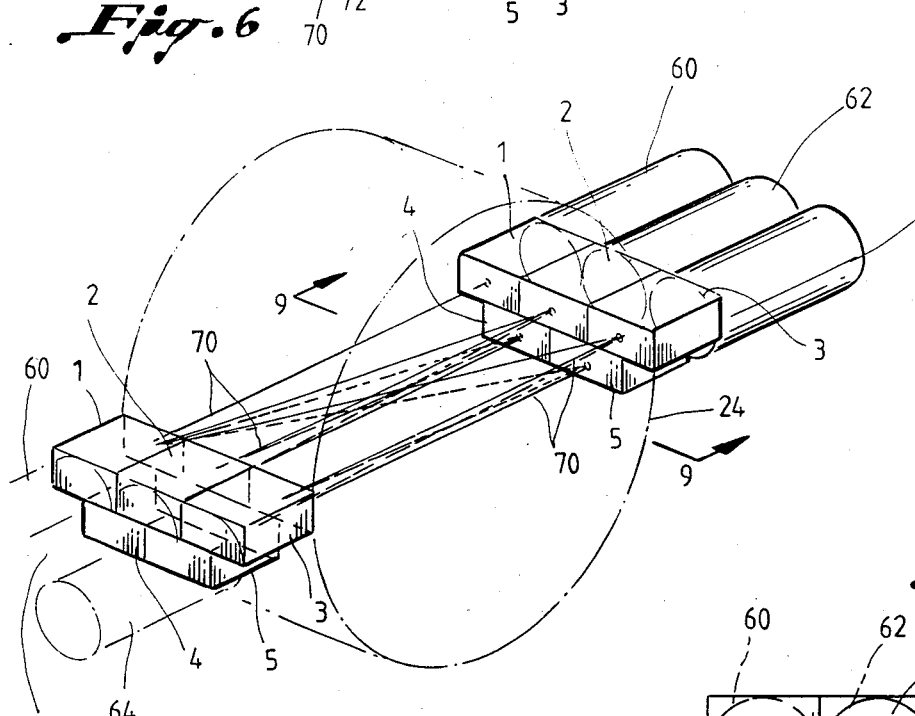
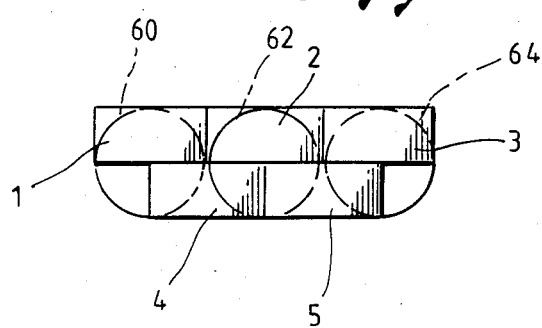

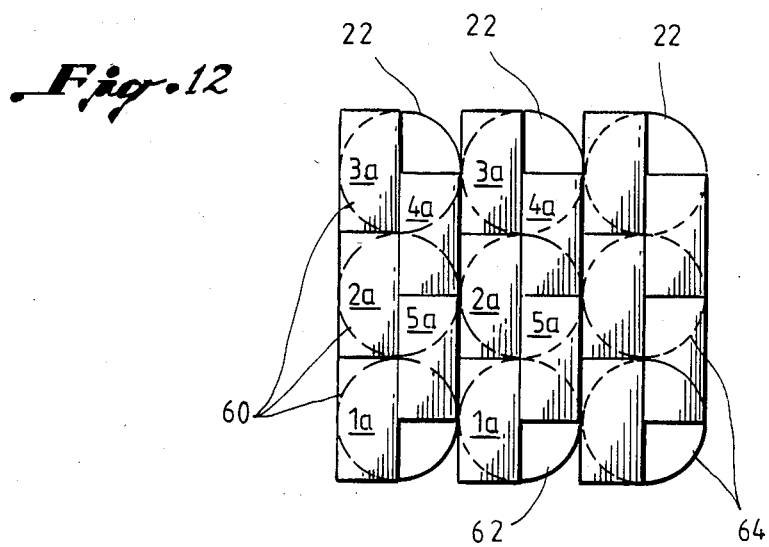
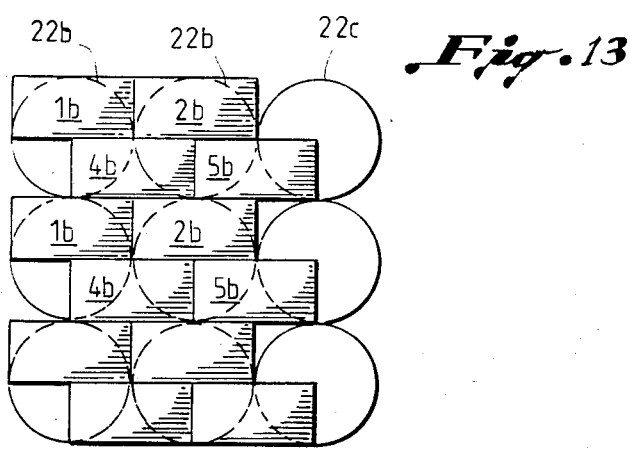
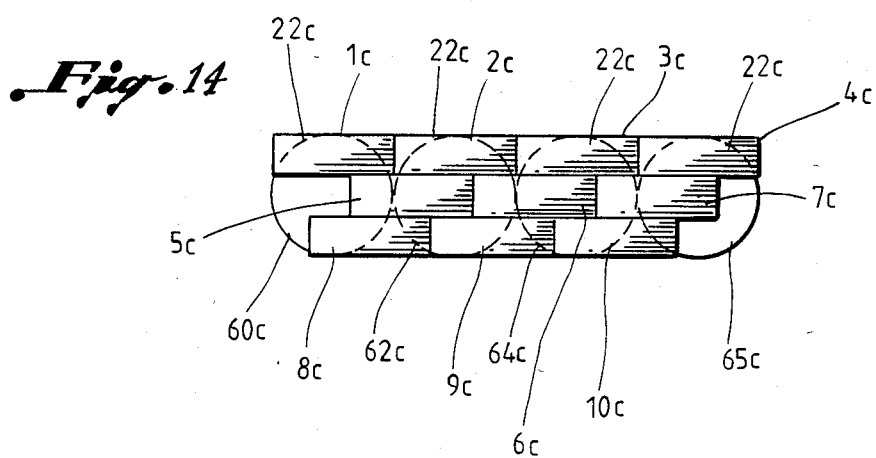

POSITRON EMISSION TOMOGRAPHY CAMERA

BACKGROUND OF THE INVENTION

The value of the positron emission tomography camera for assessing in-vivo biochemical behavior and its usefulness for clinic diagnosis of the human body is well known as set forth in my co-pending patent application Ser. No. 396,098, filed July 7, 1982, entitled Three-Dimensional Time-of-Flight Positron Emission Camera System. Conventional positron cameras are limited to planar cross-sectional imaging without using a multi-step scanning process. As the cameras become more utilized in clinical medicine, three dimensional imaging is required which has high resolution in all three dimensions, multiple image planes, and higher sensitivity. However in the past, the positron camera has been limited to a few research centers due to its high cost.

The present invention is directed to various improvements in a positron emission tomography camera which results in improved performance, high resolution, high efficiency, and lower costs.

SUMMARY

One of the major components in the cost of a positron emission tomography (PET) camera is the multitude of detectors which are formed in rings around a circumference surrounding a patient area to detect the radiation emitted by the patient. Conventional PET cameras require septas which are directional shields placed along the outer edge of each detector ring extending inwardly towards the patient to reduce the unwanted radiation and which increase the diameter of the detector rings because of their finite length. One feature of the present invention is the use of an additional septum ring placed between the conventional septas. The additional septum allows the inward extent of all of the septas to be reduced thereby reducing the diameter or inner circumference of the ring of detectors thereby reducing the number of detectors which provides a considerable reduction in the cost of the camera.

Another feature of the present invention is the offsetting of the detectors in a ring to provide better resolution, an increased number of image planes, better data sampling, and a reduction in photomultiplier tubes, and a reduction in scintillation crystal size, with a consequent reduction in cost. That is, typically detectors consist of a photomultiplier tube connected to a single scintillation crystal for detecting and converting the patient radiation into electrical pulses. However, in order to obtain higher resolution, a new feature of the present invention is positioning the crystals relative to the rings of photomultiplier tubes which allows more than one crystal to share a single photomultiplier tube and in which the crystals on one side of the photomultiplier tube are offset from the crystals on the second side of the photomultiplier tube to provide the above described advantages.

Still a further object of the present invention is the improvement in a positron emission tomography camera having a plurality of detector rings positioned side by side around a patient area to detect radiation therefrom and in which each ring has an inner circumference and each ring contains a plurality of scintillation detectors which are positioned around the circumference and are pointed inwardly for detecting radiation. A septum ring extends inwardly from the inner circumference at each outer edge of each ring for directing the area of detection of the detectors. An extra septum ring is positioned in the middle of each ring of detectors and parallel to the other septa rings and extends inwardly whereby the inward extent of all of the septa rings are reduced one-half whereby the inner circumference of the detector rings is reduced by twice the reduction in the extent of the septas thereby reducing the number of detectors required in each ring.

Yet a further object of the present invention is the improvement in a positron emission tomography camera having a plurality of detector rings positioned side by side around a patient area to detect radiation from the patient. Each ring contains a plurality of scintillation detectors pointed to the patient area and each detector ring defines a plane slice through the patient area by the detectors in each ring, and each two adjacent detector rings defines an interplane slice to the patient area. Each detector ring includes a plurality of photomultiplier tubes around the circumference and a plurality of scintillation crystals positioned around each ring. One-half of each of the multiplier tubes in each detector ring is responsive to a single crystal and the second half of each of the multiplier tubes in each detector ring is responsive to the adjacent staggered crystal which is also seen by the tube in the next ring. The crystals on the first half of the multiplier tube are offset from the crystals on the second half of the multiplier tube whereby the detectors will detect more interplane slices.

Still a further object of the present invention is wherein each ring of detectors includes a septum ring extending inwardly from the inner circumference of each outer edge of each ring and a third septum ring extends inwardly from the inner circumference and is positioned to divide the first half of each photomultiplier tube in the ring from the second half of each photomultiplier tube.

Yet a further object of the present invention is the provision of offset scintillation crystals relative to photomultiplier tubes in which a first ring of crystals is positioned on one-half of each photomultiplier tubes in each detector ring. Each crystal in the first ring is positioned on a single photomultiplier tube. A second ring of crystals is positioned on the second half of each photomultiplier tube in each ring and positioned between the crystals on the first ring. Each of the crystals on the second ring is positioned on two photomultiplier tubes in different detector rings whereby the crystals on the second ring are offset relative to the crystals on the first ring. In addition, the first ring of crystals and the second ring of crystals are aligned with the first ring of crystals and the second ring of crystals on adjacent detector rings. Because of the offset detector geometry, more interplane coincidence information can be used in the image reconstruction and therefore increasing the total sensitivity of the camera.

Another object is the provision of a first ring of crystals positioned on one-half of each photomultiplier tube in each detector ring. Each crystal in the first ring is positioned on a single photomultiplier tube. A second ring of crystals is positioned on the second half of each photomultiplier tube in each ring. Each of the crystals on the second ring is positioned on two photomultiplier tubes in the same ring whereby the crystals on the second ring are offset relative to the crystals on the first ring.

Still a further object is the provision of a plurality of rings of photomultiplier tubes in which each photomultiplier tube is responsive to third scintillation crystals.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

FIG. 1 is a perspective elevational view of the positron emission tomography camera of the present invention, FIG. 2 is a schematic cross-sectional view of the placement of a ring of detectors and septa in a conventional camera, FIG. 3 is an enlarged cross-sectional view taken along the line 3—3 of FIG. 2 showing the prior art placement of the septa relative to a detector, FIG. 3A is a cross-sectional view of the use of an additional septum of the present invention, FIG. 4 is a schematic elevational view, in cross section, illustrating the imaging of plane slices and interplane slices in a conventional positron camera, FIG. 5 is a cross-sectional view taken along the line 5—5 of FIG. 4, FIG. 6 is an elevational schematic view, in cross section, illustrating the present invention in increasing the number of plane and interplane slices being imaged, FIG. 7 is a cross-sectional view taken along the line 7—7 of FIG. 6, FIG. 8 is an elevational and schematic perspective view illustrating the plane and interplane imaging accomplished by the present invention, FIG. 9 is a cross-sectional view taken along the line 9—9 of FIG. 8, FIG. 12 is an enlarged cross-sectional view, similar to FIG. 9, of a different arrangement of detectors, FIG. 13 is an enlarged cross-sectional view, similar to FIG. 9, of a further arrangement of detectors, and FIG. 14 is an enlarged cross-sectional view, of still a further arrangement of detectors.

BRIEF DESCRIPTION OF THE PREFERRED EMBODIMENT

Figure 10:
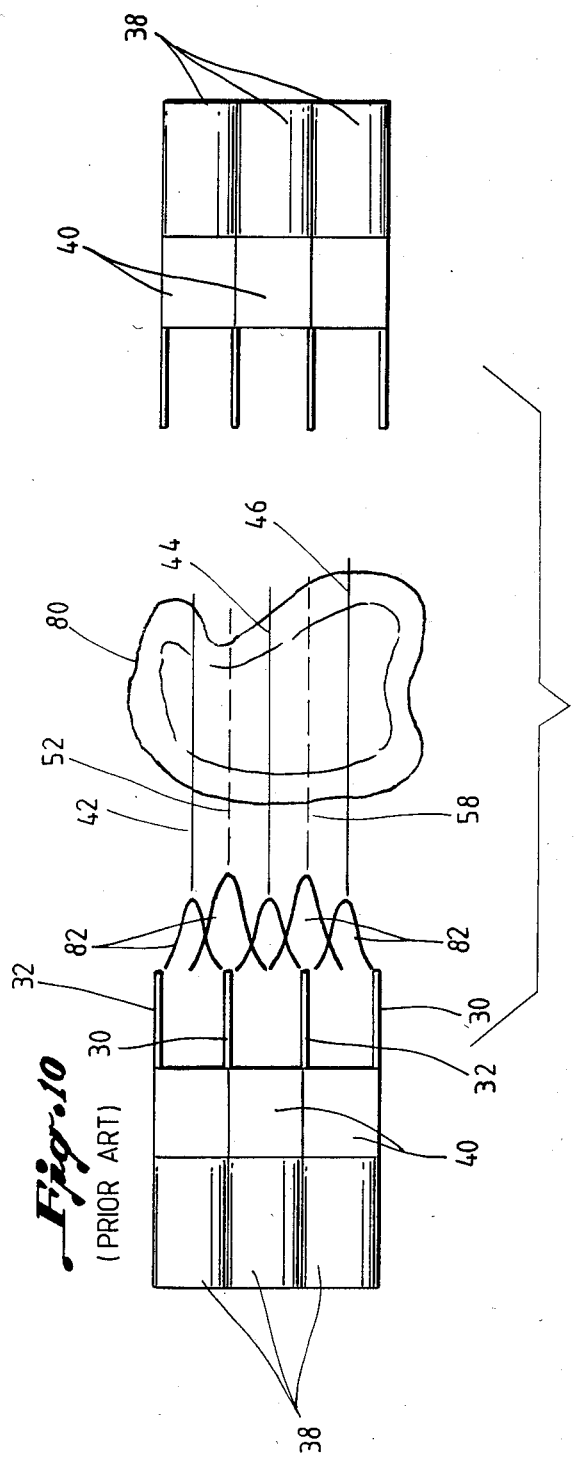
FIG. 10 is a schematic elevational view, in cross section, indicating the response obtained in a conventional positron camera.

Referring now to the drawings, and particularly to FIG. 1, the reference numeral 10 indicates a positron emission tomography camera having a support or gantry 12, a plurality of detector rings 14, here shown as three rings for convenience, positioned side-by-side around and surrounding a patient area 16 to detect radiation therefrom. The patient area may include a patient bed 18 for supporting a patient and the patient opening 16 may be tilted and the bed 18 rotated for scanning the body or an organ from several different positions. The gantry produces a wobble for increased scanning. For example only, the TOFPET I built by the University of Texas Health Science Center included five detector rings 14 each having 144 detectors for imaging nine slices simultaneously through a whole human body to detect radiation which had been injected into the body such as Rubidium-82.

Referring now to FIG. 2, a cross section of a typical positron camera has an opening 16 for insertion of the patient to be scanned, a plurality of detectors 22 for each detector ring which are mounted around the patient area 16 from an inner circumference 24 for detecting radiation from the patient area 16. Extending inwardly from the detector circumference 24 to the outside patient circumference 26 of the patient area 16 is a first 30 and second 32 septum. The septa 30 and 32 extend inwardly from the inner circumference 24 of the detector rings and from the outer edges of the detector rings 14 and are used to reduce unwanted signals such as random and scattered signals which would adversely affect the collected data. That is, septa are installed in the PET cameras to act as "blinders" for the detectors 22. Septa are normally made out of lead or tungsten and extend from the detectors 22 towards the patient.

The effectiveness of a septum is characterized by its length L, thickness and the separation S between septa. The ratio s/L defines the solid angle, or the opening of the detector 22 and determines the amount of scattered and random radiation reaching the detectors 22.

One of the major components in the cost of a PET camera is the numerous detectors 22 which must extend around and cover the inner circumference 24 in order to pick up the radiation being emitted in all circumferential directions. The diameter D of the detector inner circumference 24 is determined by the diameter d of the patient opening 16, the septa length L and the wobble diameter w.

Therefore, diameter $D = d + 2L + 2w$.

And the number of detectors in a detector ring 14 is given by the formula:

$(\pi D)/\text{size of detector}$

Therefore, if D can be reduced, then the number of detectors 22 can be reduced and the cost of the camera can be lowered. For some applications, the patient opening d may be reduced such as when the camera 10 is to be used for imaging of only the brain instead of any part of a whole body.

One feature of the present invention is the provision of an extra septum 36 which, as best seen in FIG. 3A, is placed in between the position of the normal septa 30a and 32b which allows the total length of all of the septa to be reduced to approximately L/2. The scattered and random signals are still maintained at approximately similar levels to the prior art structure of FIG. 3, but the sensitivity of the detectors 22 is slightly increased since the outer circumference 24 will be reduced by the distance L allowing the detectors 22 to be closer to the object being imaged. By way of example only, for a whole body camera the diameter D of the inner circumference ring 24 can be reduced from 100 centimeters to 80 centimeters for a 20% decrease in the number of detectors 22. This can result in a cost savings of approximately twenty percent in the cost of the detectors.

Referring to FIGS. 3 and 3A, typically a detector 22 consists of a photomultiplier tube 38 and a scintillation crystal 40. The crystal 40 converts the detected radiation into light which is transmitted to the photomultiplier tube 38 for converting the detected radiation into electrical pulses.

That is, typically, for a single tube 38, a single crystal 40 is connected thereto. Referring to FIGS. 4 and 5, a typical prior art camera is shown having three rings of detectors 22, each detector 22 including a photomultiplier tube 38 with a single crystal 40 with extending septa 30 and 32. Such a conventional type arrangement provides a total of five slices or images through the patient's body. That is, detectors 22 which are opposite to each other will provide "straight on" slices 42, 44 and 46. Interplane slices are detected such as interplane slices 48 and 50 which when added together provided a single "in between" slice 52. Similarly, cross slices 54 and 56 when added together provided an "in between" slice 58. Thus prior art cameras provided slices equal to two times the number of rows n of detectors minus 1.

In order to obtain higher resolution in positron cameras, the detectors have been made smaller, but the number and size of the detectors becomes restrictive. Another feature of the present invention has been provided which allows sharing of one photomultiplier tube by more than one scintillation crystal in which the crystals are positioned for ease of identification, also the number of image planes is increased, the effective detector size is made smaller so that resolution is improved by a factor of approximately two, but the cost of the camera is reduced because approximately one-half the total number of photomultiplier tubes are required as compared to the conventional mode.

Referring now to FIGS. 8 and 9, in which photomultipliers 60, 62, and 64 are shown which are in different rows 14 in the camera 10. In addition, a plurality of scintillation crystals, any suitable crystal is satisfactory, are positioned around the internal circumference 24 of the detectors for detecting radiation from the patient area which the crystals convert into light and the photomultipliers convert into electrical pulses. The crystals are positioned relative to the photomultiplier tubes 60 and 62 and 64 whereby each multiplier tube is responsive to more than one crystal. Thus crystals 1, 2 and 3 are seen only by photomultiplier tubes 60, 62 and 64, respectively. Crystals 1, 2 and 3 cover one-half, such as the upper half, of each of the photomultipliers in each of the rows 14. However, crystal 4 is positioned adjacent to and is seen by photomultiplier tubes 60 and 62 while crystal 5 is seen by multiplier tube 62 and 64. With this arrangement, the identification of the crystal can readily be made. That is, if crystal 1 is actuated only photomultiplier 60 is responsive. Similarly, if crystal 2 is actuated only photomultiplier 62 is responsive, and if crystal 3 is actuated only photomultiplier 64 is responsive. However, if both photomultiplier 60 and 62 resond, this is an identification of crystal 4. Similarly, crystal 5 will create a response in both photomultiplier tubes 62 and 64. This structure also provides greater resolution as the size of the crystals 1, 2, 3, 4 and 5 are made smaller than the normal crystal size by a factor of 2 as a normal crystal will cover the entire face of the photomultiplier tube. This structure and method also requires fewer multiplier tubes by almost one-half for detecting identification of the crystals. Costs are reduced as the smaller size crystals are less expensive than the larger size crystals. In addition, better data sampling is provided in the slice direction.

Another important feature of the arrangement of the crystals relative to the photomultiplier tubes is the fact that the number of image planes is increased because of the improved sampling of the data provided by the offsetting of the first set of crystals 1, 2 and 3 relative to the second set of crystals 4 and 5. FIGS. 4 and 5 indicated that a three row detector camera will provide three straight-on slices and two effective in-between slices. However, the present improvement, as best seen in FIGS. 6 and 7, will because crystals 4 and 5 are offset, and behind in dotted outlines, the crystals 1, 2 and 3, will provide nine effective slices consisting of five straight on slices and four effective "in between" slices. The straight-on slices are numbered 70 and the effective in-between slices are numbered 72.

Figure 11:
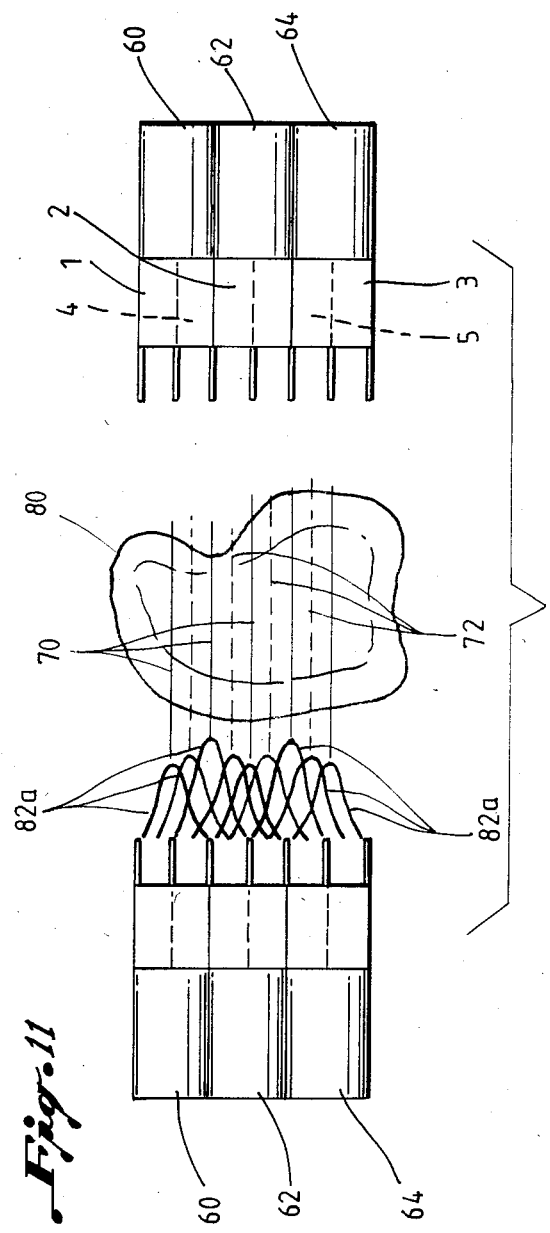
FIG. 11 is a schematic elevational view, in cross section, of the increased response accomplished by the present invention.

The advantages of the additional slices in the accuracy of the measured radiation is best seen by referring to FIGS. 10 and 11. FIG. 10 is the prior art structure of FIGS. 4 and 5.

It is to be noted that the usable data obtained from the slices 42, 44, 46, 52 and 58 as indicated by the response curves 82 leave a considerable number of gaps between the response curves 82. On the other hand, referring to the structure of the present invention as best seen in FIG. 11, the greater number of response curves 82a are closer together thus presenting a more complete scan of the area of the patient 80.

It is to be noted that while the feature of the additional septa as described in connection with FIGS. 1-3A may be used with the feature of identifying the offset scintillation crystals as described in connection with FIGS. 4-9, the two features may be used separately or together if desired.

Referring now to FIG. 12, a different arrangement of detectors is best seen. In this embodiment detector rings 22 are provided in which the different rings include photomultiplier tubes 60, 62, 64, respectively. In this embodiment, the arrangement of crystals 1a, 2a, 3a, 4a, and 5a are rotated ninety degrees compared to the embodiment of FIG. 9. The arrangement of FIG. 12 provides similar identification of the crystals and advantages of the arrangement of FIG. 9, but in FIG. 12 the in-plane slices are thinner and high interplane resolution is obtained.

Referring now to FIG. 13, a still different detector arrangement is provided in which rings 22b are shown. In this embodiment crystals 1b, 2b, 4b and 5b are provided. This arrangement with less crystals is not as efficient although the offset rows of crystals are advantageous over the conventional detectors in some respects.

Referring now to FIG. 14, an arrangement is provided in which the rings 22c contain photomultiplier tubes 60c, 62c, 64c, and 65c, respectively, which are responsive to the three crystals. The crystals are 1c, 2c, 3c, 4c, 5c, 6c, 7c, 8c, 9c, and 10c which are positioned in horizontal rows across the rings 22c. If desired, the crystals could be positioned around each of the rings 22c instead of across the plurality of rings 22c. Thus crystal 1c is identified by a signal from only tube 60c. Crystal 5c is identified by a signal of tube 62c being larger than a signal from tube 60c. Similarly crystal 8c is identified by a signal from tube 60c being larger than a signal from tube 62c. Identification of the other crystals is similar.

The embodiment of FIG. 14 has the advantages of higher resolution, more effective sampling in the image planes, and lower costs because of sharing of the photomultiplier tubes.

In use, the positron emission tomography camera of the present invention provides a higher resolution, increased number of image planes, requires less photomultiplier tubes, provides better data sampling in the slice direction, has fewer gaps, the whole object is sampled in three dimensions for accurate representation, and this is accomplished at less cost.

The present invention, therefore is well adapted to carry out the objects and attain the ends and advantages mentioned as well as others inherent therein. While a presently preferred embodiment of the invention is given for the purpose of disclosure, numerous changes in the details of construction and arrangement of parts will readily suggest themselves to those skilled in the art and which are encompassed within the spirit of the invention and the scope of the appended claims.

What is claimed is:

1. In a positron emission tomography camera having a plurality of detector rings positioned side-by-side around a patient area to detect radiation therefrom, each ring having an inner circumference and each ring containing a plurality of scintillation detectors which are positioned around the circumference and are pointed inwardly for detecting radiation and a septa ring extending inwardly from the inner circumference of each outer edge of each ring for directing the area of detection of said detectors, the improvement in means for reducing the inward extent of said septa rings thereby reducing the diameter of said inner circumference of detectors and reducing the number of detectors required in each ring comprising, an extra septa ring positioned in the middle of each ring of detectors and parallel to the other septa rings and extending inwardly and the inward extent of all of the septa rings are equal whereby the inner circumference of the detector rings is reduced by the reduction in the inward extent of said septa rings.

2. In a positron emission tomography camera having a plurality of detector rings positioned side-by-side around a patient area to detect radiation therefrom, each ring having an inner circumference and each ring containing a plurality of scintillation detectors which are positioned around the circumference and are pointed inwardly for detecting radiation and a septa ring extending inwardly from the inner circumference of each outer edge of each ring for directing the area of detection of said detectors, the improvement in means for reducing the inward extent of said septa rings thereby reducing the diameter of said inner circumference of detectors and reducing the number of detectors required in each ring comprising, an extra septa ring positioned in the middle of each ring of detectors and parallel to the other septa rings and extending inwardly whereby the inward extent of all of the septa rings are reduced one-half whereby the inner circumference of the detector rings is reduced by the reduction in septa extent.

3. In a positron emission tomography camera having a plurality of adjacent detector rings positioned side-by-side around a patient area to detect radiation from the patient, each ring containing a plurality of scintillation detectors pointed to the patient area, each detector ring defining a plane slice through the patient area by the detectors in each ring, and each two adjacent detector rings defining an interplane slice through the patient area, the improvement in the rings of detectors comprising, each detector ring including a plurality of photomultiplier tubes around the circumference, a plurality of scintillation crystals positioned around each ring adjacent the photomultiplier tubes for detecting radiation from the patient area which the tubes convert into electrical pulses, said crystals positioned relative to the photomultiplier tubes whereby each photomultiplier tube is responsive to more than one crystal, each multiplier tube has one-half of the tube responsive to a single crystal, and the second half of the tube is responsive to two different crystals, and the crystals on the one-half of each tube are offset from the crystals on the second half of the same tube such that the detectors detect more interplane slices.

4. In a positron emission tomography camera having a plurality of adjacent detector rings positioned side-by-side around a patient area to detect radiation from the patient, each ring containing a plurality of scintillation detectors pointed to the patient area, each detector ring defining a plane slice through the patient area by the detectors in each ring, and each two adjacent detector rings defining an interplane slice through the patient area, the improvement in the rings of detectors comprising, each detector ring including a plurality of photomultiplier tubes around the circumference, a plurality of scintillation crystals positioned around each ring adjacent the photomultiplier tubes for detecting radiation from the patient area which the tubes convert into electrical pulses, said crystals positioned relative to the photomultiplier tubes whereby each photomultiplier tube is responsive to more than one crystal, a first ring of crystals in each detector ring is positioned on one half of said photomultiplier tubes, each crystal in said first ring being positioned adjacent a single photomultiplier tube, and a second ring of crystals in each detector ring is positioned on the second half of said photomultiplier tubes, each of the crystals in the second ring being positioned adjacent to two photomultiplier tubes whereby the crystals in the second ring are offset relative to the crystals in the first ring.

5. In a positron emission tomography camera having a plurality of adjacent detector rings positioned side-by-side around a patient area to detect radiation from the patient, each ring containing a plurality of scintillation detectors pointed to the patient area, each detector ring defining a plane slice through the patient area by the detectors in each ring, and each two adjacent detector rings defining an interplane slice through the patient area, the improvement in the rings of detectors comprising, each detector ring including a plurality of photomultiplier tubes around the circumference, a plurality of scintillation crystals positioned around each ring adjacent the photomultiplier tubes for detecting radiation from the patient area which the tubes convert into electrical pulses, said crystals positioned relative to the photomultiplier tubes whereby each photomultiplier tube is responsive to more than one crystal, a first septa ring extending inwardly from the inner circumference on one side of each ring of detectors, a second septa ring extending inwardly from the inner circumference on the second side of each ring of detectors, and a third septa ring extending inwardly from the inner circumference between the first and second septa rings.

6. The apparatus of claim 5 wherein the third septa ring is positioned to divide the first half of each photomultiplier tube in the ring from the second half of each photomultiplier tube.

7. In a positron emission tomography camera having a plurality of adjacent detector rings positioned side-by-side around a patient area to detect radiation from the patient, each ring containing a plurality of scintillation detectors pointed to the patient area, each detector ring defining a plane slice through the patient area by the detectors in each ring, and each two adjacent detector rings defining an interplane slice through the patient area, the improvement in the rings of detectors comprising, each detector ring including a plurality of photomultiplier tubes around the circumference, a plurality of scintillation crystals positioned around each ring adjacent the photomultiplier tubes for detecting radiation from the patient area which the tubes convert into electrical pulses, said crystals positioned relative to the photomultiplier tubes whereby each photomultiplier tube is responsive to more than one crystal, a first ring of crystals is positioned in each detector ring on one-half of said photomultiplier tubes, each crystal in said first ring being positioned on a single photomultiplier tube in a single detector ring, a second ring of crystals positioned in each detector ring on the second half of said photomultiplier tubes and positioned between the crystals on the first ring, each of the crystals on the second ring being positioned on two photomultiplier tubes in different detector rings whereby the crystals on the second ring are offset relative to the crystals on the first ring, said first ring of crystals and said second ring of crystals being aligned with the first ring of crystals and the second ring of crystals on adjacent detector rings.

* * * * *